(12) United States Patent
Colin et al.

(10) Patent No.: US 6,271,407 B1
(45) Date of Patent: Aug. 7, 2001

(54) PREPARATION OF HYDROGENOSILANES BY CATALYTIC HYDROGENOLYSIS OF POLYSILANES

(75) Inventors: Pascale Colin, Chassieu; Claude De Bellefon, Meyzieu; Christina Garcia-Escomel, Lyons; Pierre Grenouillet, Fontaines-sur-Saône; Philippe Morel, Chuzelles, all of (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/647,996

(22) PCT Filed: Apr. 2, 1999

(86) PCT No.: PCT/FR99/00771

§ 371 Date: Jan. 25, 2001

§ 102(e) Date: Jan. 25, 2001

(87) PCT Pub. No.: WO99/51611

PCT Pub. Date: Oct. 14, 1999

(30) Foreign Application Priority Data

Apr. 7, 1998 (FR) .................................................. 98 04600

(51) Int. Cl.$^7$ ....................................................... C07F 7/08
(52) U.S. Cl. ............................................................ 556/468
(58) Field of Search ............................................... 576/468

(56) References Cited

U.S. PATENT DOCUMENTS

| | | | |
|---|---|---|---|
| 4,079,071 | * 3/1978 | Neale | 556/468 |
| 5,175,329 | * 12/1992 | Bokerman et al. | 556/468 |
| 5,922,893 | * 7/1999 | Tsukono et al. | 556/468 |
| 6,013,824 | * 1/2000 | Wood | 556/468 |

FOREIGN PATENT DOCUMENTS

| | | | |
|---|---|---|---|
| 0700920 | * 3/1996 | (EP) | . |
| 2239474 | * 2/1975 | (FR) | . |
| 2342981 | * 9/1977 | (FR) | . |

* cited by examiner

Primary Examiner—Paul F. Shaver
(74) Attorney, Agent, or Firm—Burns, Doane, Swecker & Mathis, L.L.P.

(57) ABSTRACT

The invention concerns a method for preparing hydrogenated alkylmonosilanes, by catalytic hydrogenolysis, under hydrogen pressure, of halogenoorganopolysilanes, improving known methods, in particular by facilitating implementation, and in terms of cost-effectiveness and performance which are shown by the efficiency of the resulting hydrogenated monosilanes. In said method the starting polysilanes are of the type: $(CH_3)Cl_2Si-SiCl(CH_3)_2$; $(CH_3)Cl_2Si-SiCl_2(CH_3)$; $(CH_3)Cl_2Si-Si(CH_3)_3$; $(CH_3)_2ClSi-SiCl(CH_3)_2$; $(CH_3)Cl_2Si-SiCl(Ch_3)-SiCl_2(CH_3)$; $(CH_3)Cl_2Si-Si(CH_3)(SiCH_3Cl_2)-SiCl_2CH_3$. The hydrogenated monosilanes $CH_3H_2ClSi$; $(CH_3)_2HClSi$; $CH_3HCl_2Si$ are obtained by contacting said polysilanes with gaseous hydrogen under pressure, in the presence of a catalytic system AB comprising a hydrogenation catalyst precursor A and an auxiliary B for dissolving precursor A in the reaction medium. Said catalytic system is further characterized in that it is reductant-free.

15 Claims, No Drawings

PREPARATION OF HYDROGENOSILANES BY CATALYTIC HYDROGENOLYSIS OF POLYSILANES

The field of the invention is that of the production of hydroalkylsilanes from polysilanes and in particular disilanes.

More specifically, a subject-matter of the invention is a process for the preparation of hydrohaloalkylsilanes by catalytic hydrogenolysis of the Si—Si bond of haloalkylpolysilanes with gaseous hydrogen under pressure.

In the silicone industry, organohalosilanes (that is to say, in practice, methylchlorosilanes) are the fundamental units involved in the construction of silicone polymers (polyorganosiloxanes, POSs). Methylchlorosilanes are virtually always manufactured by direct synthesis (Rochow-Müller synthesis) with silicon and methyl chloride. This synthesis results in $(CH_3)_2SiCl_2$ (65–85%), $CH_3SiCl_3$ (7–18%), $(CH_3)_3SiCl$ (2–4%), $CH_3SiHCl_2$ (0.5%) and polysilanes (6–8%).

These polysilanes are compounds of high boiling point which constitute the heavy fractions of the distillations carried out in order to separate the various monomers produced by direct synthesis. These polysilanes comprise disilanes which are: $(CH_3)Cl_2Si$—$SiCl(CH_3)_2$; $(CH_3)Cl_2Si$—$SiCl_2(CH_3)$; $(CH_3)Cl_2Si$—$Si(CH_3)_3$; $(CH_3)_2ClSiSiCl(CH_3)_2$, denoted respectively by $Me_{12}$, $Me_{11}$, $Me_{13}$ and $Me_{22}$, each figure in these indices corresponding to the number of methyl substituents carried by either one of the silicon atoms of the disilanes. $Me_{12}$, $Me_{11}$ and $Me_{13}$ are also known as "cleavable" disilanes. They represent 80% of the heavy fraction, against 10% for $Me_{22}$; approximately 10% of the mass being composed of products comprising Si—O—Si and Si—$CH_2$—Si units.

One of the routes for enhancing in value these disilanes involves their conversion into hydrogenated organohalosilanes: dichloromethylhydrosilanes (MeH), monochlorodimethylhydrosilanes ($Me_2H$) or chloromethyldihydrosilane ($MeH_2$).

A particularly advantageous outlet for these hydrogenated haloorganosilanes, such as hydrogenated chloromethylsilanes, is the functionalization of polyorganosiloxanes and in particular those obtained from the dimethyldichlorosilane monomer. By hydrolysis and condensation, MeH, $MeH_2$ and $Me_2H$ can be integrated into silicone backbones to form monohydrogenated and dihydrogenated siloxyl units D ($SiO_{2/2}$) and monohydrogenated siloxyl units M ($SiO_{1/2}$).

Haloorganosilanes are also reaction intermediates which can be used in the preparation of polysilanes by the formation of an Si—Si bond via a dehydrogenation. Another application of hydrogenated haloorganosilanes can be the hydrosilylation of organic compounds.

The present invention relates to the problem of producing, in a simple and profitable way, hydrogenated haloorganosilanes by catalytic hydrogenolysis of polysilanes.

The catalytic hydrogenolysis of the Si—Si bonds of polysilanes of the heavy fraction from direct synthesis represents the most advantageous option of the prior art for enhancing in value. It makes it possible to convert by-products of low added value into reaction intermediates of high added value.

Two types of catalytic hydrogenolysis of polysilanes are distinguished according to the hydrogen source used, namely either hydrochloric acid in solution or gaseous hydrogen under pressure.

The process disclosed in Patent FR 1,447,304 relates to the first type of catalytic hydrogenolysis. The reaction which governs the process according to this patent is as follows:

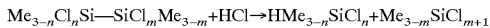

$Me_{3-n}Cl_nSi$—$SiCl_mMe_{3-m}+HCl \rightarrow HMe_{3-n}SiCl_n+Me_{3-m}SiCl_{m+1}$ The catalyst employed is chosen from amides or organic bases. This process suffers from two major disadvantages. The first is related to the stoichiometry of the reaction, according to which, per mole of disilane, only one mole of hydrogenated chloromethylsilane is obtained. The second disadvantage is related to the specificity of the catalysts used in this type of process. This is because the said catalysts are preferably active with respect to disilanes comprising at least one monoalkylated fragment ($MeCl_2Si$) at the expense of the disilanes which do not comprise it.

There exist several prior technical proposals in which the reaction chamber is fed with gaseous hydrogen under pressure. All these proposals have cumbersome and drastic operating conditions in common.

In this mood, French Patent No. 2,085,143 discloses the hydrogenolysis of disilanes $Me_{12}$ in the presence of an organometallic catalyst composed of a complex palladium salt, bis(tributylphosphine)dichloropalladium $(PBu_3)_2PdCl_2$.

This hydrogenolysis catalyst is employed in a proportion of 1% by weight. The hydrogen pressure of $211\times10^5$ Pa employed is so high that it is out of the question on an industrial scale. The reaction temperature is relatively high: 120° C. The nevertheless lengthy reaction time does not make it possible to obtain high conversion ratios (74%). Finally, it should be emphasized that the starting materials are not composed of a mixture of polysilanes but of a single disilane.

U.S. Pat. No. 4,079,071 teaches, for its part, the hydrogenolysis of a mixture of disilanes $Me_{11}$, $Me_{12}$, $Me_{22}$, $Me_{13}$ and $Me_{23}$ in the presence of 1% of hydrogenolysis catalysts formed by bis(tributylphosphine)dichloronickel $(Pbu_3)_2NiCl_2$ at a temperature of 150° C. under a hydrogen pressure of $50\times10^5$ Pa for 6 hours. Here again, it should be noted that, from an industrial viewpoint, these are not ideal operating conditions.

U.S. Pat. No. 5,175,329 discloses a process for the conversion of polysilanes, formed by a mixture of disilanes $Me_{13}+Me_{22}+Me_{12}+Me_{11}$ with methyltrichlorosilanes added, into hydrogenated or nonhydrogenated monosilanes. This conversion is carried out using a hydrogenolysis catalyst chosen from nickel-, palladium- or platinum-based organometallic compounds or from complex salts of these same metals. One example given for this catalyst is bis(tributylphospine)dichloronickel: $(PBu_3)_2NiCl_2$. According to one alternative form, the hydrogenolysis catalyst can be composed of inorganic forms of these metals, Ni, Pd and Pt, attached, for example, to a support of the alumina type. The redistribution catalyst is chosen from quaternary phosphonium or ammonium halides or aluminium or boron halides. It can be, for example, a tetrabutylphosphonium chloride. The hydrogenolysis is carried out at 135° C. under a hydrogen pressure of $36\times10^5$ Pa for very long periods of time, which can reach 17 hours, for a yield of hydrogenated monosilanes with respect to all the silicon involved of the order of 40%. In the light of such results, it is difficult to maintain that this prior process is economically viable on an industrial scale.

French Patent No. 2,342,981 is targeted at the hydrogenolysis of mixtures of disilanes of the type of those comprising 81% of tetrachlorodimethyldisilane ($Me_{11}$), 17% of trichlorotrimethyldisilane ($Me_{21}$) and 2% of dichlorodimethyldisilane (Me$_{22}$) in the presence of a catalyst formed by an aprotic base of the hexamethylphosphoric triamide (HMPT) type and by divided nickel obtained by prior or in situ reduction of an inorganic or organic derivative (cyclopentadienylnickel or nickelocene) by a reducing agent or by hydrogen. The reaction is carried out under a hydrogen pressure of 25×10$^5$ Pa at 110° C. The reaction time is less than 1 hour for a conversion of the order of 70% and a selectivity for hydrogenated monosilanes of the order of 56%. In this instance, the operating conditions are milder and therefore more acceptable but the performance in terms of conversion and selectivity is very inadequate.

In this process, the examples given show that the catalyst is formed either by use of a sophisticated and expensive organometallic nickel compound or by reduction of nickel chloride by a further addition of a powerful and expensive reducing agent, such as triethylsilane.

In such a technical environment, one of the essential objectives of the present invention is to provide a process for the preparation of hydrogenated alkylmonosilanes, by catalytic hydrogenolysis under hydrogen pressure of haloorganopolysilanes, which improves the known processes, in particular in terms of ease of implementation, of profitability and of performance, expressed, for example, through the yield of hydrogenated monosilanes produced.

Another essential objective of the present invention is to provide a process for the production of hydrogenated alkylmonosilanes, for example of methylhydrosilanes, which is efficient and of high performance for a large variety of starting polysilanes, which can equally well comprise a given polysilane of any type and a mixture of several polysilanes.

Another objective of the present invention is to provide an improved process for the preparation of hydrosilanes from polysilanes, by catalytic hydrogenolysis under hydrogen pressure, which does not involve starting materials, reaction intermediates or coproducts which are dangerous to handle and/or toxic, such as phosphorus compounds.

Having been set these objectives, the inventors have had the credit of envisaging the desired improvement from the viewpoint of optimizing the specific catalytic system for reactions for the hydrogenolysis of polysilanes, in particular of disilanes, to hydrogenated or nonhydrogenated monosilanes. Thus it is that, surprisingly and unexpectedly, a novel catalytic system has been discovered which is very selective and very active for the production of hydromethylchlorosilanes and which is obtained by reduction, in the reaction medium (in situ), of simple transition metal salts not comprising ligands capable of stabilizing or of complexing the metal in a degree of oxidation required for the activation of molecular hydrogen (zero or one), this class of undesired ligands being well defined in the sense of the coordination chemistry of these metals, it being necessary for these simple salts to be used in combination with dissolution aids chosen from nucleophiles which are soluble in an aprotic medium.

It follows that a subject-matter of the present invention is a process for the preparation of hydrosilanes from polysilanes, in which gaseous hydrogen under pressure is brought into contact with polysilanes of formula (I):

$$R_aH_bSi_nX_{2n+2-a-b} \quad (I)$$

in which:
the R radicals are identical or different and are chosen from a group comprising:
linear or branched $C_1$–$C_6$ alkyls, aryls, linear or branched $C_1$–$C_6$ alkoxyls, a trifluoropropyl radical or a trimethylsiloxyl radical the X radicals are halogens which are identical to or different from one another
n=2 to 20
a=0 to 2n+2
b=0 to 2n+2
a+b=0 to 2n+2
in order to obtain monosilanes of formula (II):

$$R_cH_dSiX_{4-c-d} \quad (II)$$

in which:
R and X are as defined above
c=1, 2, 3 or 4
d=0, 1 or 2
c+d=2, 3 or 4
characterized in that polysilane (I) and hydrogen are brought into contact in the presence of a catalytic system comprising
—A— on the one hand, at least one precursor of at least one hydrogenation catalyst, this precursor A being chosen from salts of at least one transition metal, the anionic or neutral ligands of which are devoid of π-acceptor orbitals, halides and in particular chlorides being very particularly preferred ligands,
—B— and, on the other hand, at least one aid for dissolution of the precursor A in the reaction medium, this aid B being selected from nucleophiles which are soluble in an aprotic medium, with or without the exception of HMPT, preferably from salts comprising anionic or neutral ligands which are devoid of π-acceptor orbitals, halides of soluble nature and in particular chlorides being particularly preferred;
with the exclusion of a reducing agent.

The catalytic system AB according to the invention has significant advantages, in particular with regard to the operating conditions. This is because the reaction temperature can be lowered below 100° C. without resulting in an excessive increase in the reaction time necessary and sufficient in order to obtain conversions of substrates of greater than 95% and yields of hydrogenated products of 70%. In practice, these times are less than 8 h and more conventionally between 0.1 and 4 hours.

In addition, by virtue of the catalytic system AB according to the invention, very high hydrogen gas pressures, which require sophisticated and expensive equipment, may be dispensed with. For example, hydrogen pressures $P_{H_2}$ of 30×10$^5$ Pa or less are entirely suitable.

Furthermore, the process according to the invention is advantageous as it more than meets the minimum required as regards the safety of its implementation and the toxicity of the products concerned.

This process is also of high performance economically, due to the fact that is does not require complex and expensive equipment and that the consumables which are required, in particular the catalyst, are inexpensive in the amounts employed.

To summarize, the process according to the invention is particularly advantageous as it makes it possible to achieve better selectivities for hydrogenated monosilanes with good yields and under conditions of low pressure, of low temperature and of low concentration of catalytic metal.

Preferably, the polysilanes to which the invention more particularly but not in a limiting way relates are chloromethyldisilanes.

The catalyst A selected according to the invention is generated from a simple salt of at least one transition metal which is non-complexed with ligands possessing π-acceptor properties within the sense of the coordination chemistry of these metals. Furthermore, this salt has to be sufficiently soluble in the reaction medium, which is preferably an aprotic medium, for the metal in the liquid oxidized form to be able to change into a reduced form (degree of oxidation= 0), which corresponds to the state in which it is active as catalyst. The fact of having been able to discover this discriminating criterion for the selection of appropriate catalysts is the product of a particularly inventive process of reasoning which is to the credit of the inventors. The latter have thus proposed the selection of transition metal salts in which the coordination sphere of the metal does not comprise excessively strong ligands (non-π-acceptor ligands), so as to optimize the availability of the metal in the catalytically active form.

The appropriate ligands are those which do not comprise π-acceptor orbitals. These π-acceptor ligands, which are to be excluded in accordance with the invention, are defined in "Cotton, F. A. and Wilkinson, G, *Advanced Inorganic Chemistry*, 4th Ed., 1980, John Wiley & Sons, New York (Chapters 3 and 4 and more particularly pages 81–82 and 95)", "Wilkinson G., *Comprehensive Coordination Chemistry*, Pergamon Press, Oxford, 1987, Vol. 5, (Chap. 50 §50.2.2)" or "Wilkinson, G., *Comprehensive Coordination Chemistry*, Pergamon Press, Oxford, 1987, Vol. 4. Chap. 44".

According to a preferred characteristic of the invention, the non-π-acceptor ligands which can be selected as counteranions of transition metal salts of the catalyst A are halides and more preferably still chlorides.

These chlorides have the not insignificant advantage of being nontoxic.

According to another advantageous arrangement of the invention, it is seen to that the metal or metals included in the catalyst A belong to the following group:

Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pr and Au, and preferably to the following subgroup:

Pt, Ti, Cr, Mn, Fe, Cu, Ag, Au and Ni; the latter being particularly preferred.

In a non-limiting way, the process according to the invention encompasses the case where the transition metal salt A is incorporated into the reaction medium at the start of the catalytic hydrogenolysis reaction and also the case where it is seen to that the conditions are brought together in order for the simple and soluble salt A of at least one transition metal to be formed in situ from a corrodable metallic precursor, which may or may not be supported, subjected to the corrosive action of at least one acid capable of providing the non-π-acceptor ligand or ligands for the salt A, the metallic precursor advantageously being chosen from the following metals: Co, Fe, Ni, Pd, Pt or Cu.

This alternative form, which involves an in situ formation of the catalyst A, can consist in bringing the bulk metal, finely divided or supported on a solid support, such as alumina, silica, active charcoal, and the like, into contact with the appropriate acid in order to generate the salt A by corrosion of the metal, it being known that this salt must comprise a non-π-acceptor ligand.

The preferred embodiment of the process according to the invention remains, all the same, that according to which the simple salt of the transition metal is incorporated into the starting reaction medium.

In any case, whatever the method of introducing the catalyst A, the selection of the catalyst A will be favoured, in accordance with the invention, from the group of salts comprising: $NiCl_2$, $CuCl_2$ and $FeCl_2$; $NiCl_2$ being very especially preferred.

As regards the aid B for dissolution of the hydrogenation catalyst A, it should be specified first of all what the notion of solubility covers within the meaning of the present invention.

Thus, it is well known that simple salts of transition metals, particularly halides, exist in polymeric or oligomeric form in the solid state. The reaction of the dissolution aid has the effect of breaking this chain and of generating much more soluble mono- or dimeric species. These complex transition metal species are generally coloured and their dissolution in the polysilane or disilane medium can easily be confirmed, for example, by ultraviolet/visible spectroscopy.

The aid B has the precursor function of upgrading the activity of the catalyst A by promoting the dissolution of its precursor salt in the reaction medium while facilitating the change of the transition metal into an active reduced form. The aid B also contributes to the mechanism for cleaving the Si—Si bonds.

For the aid B, the best results are obtained with compounds which are not π-acceptor ligands, such as, for example, halides which are soluble and more particularly still chlorides. Mention may be made, among soluble halides, as non-limiting examples, of phosphonium, ammonium, imidazolium or pyridinium halides or alkali metal and alkaline earth metal halides, the cation of which is hidden by crown ethers or other cryptands, as described in the specialist technical literature.

However, in addition to the halides, which are preferred, the use is not excluded as dissolution aid of π-acceptor ligands, such as phosphines $PR_3$ (R=alkyl, aryl, and the like), phosphites $P(OR)_3$ and their oxides, amines, amides or pyrrolidones, olefins, diolefins or polyolefins, nitrites, isonitriles and any other compound capable of helping in the dissolution, as described in the present invention, of the transition metal salt.

The aids B which may be favoured in practice are:

$NBu_4Cl$; $PBu_3$; $[(Ph)_3P=N=P(Ph)_3]Cl$;

Bu=butyl, Ph=phenyl

Quantitatively, the catalyst A represents from 0.01 to 5% by weight, preferably from 0.01 to 1% by weight, with respect to the reaction medium.

The concentrations of the aid B vary for their part from 0.1 to 10% by weight, preferably, and more preferably still from 1 to 7% by weight with respect to the reaction medium.

As regards the other operating parameters, the hydrogen gas pressure $P_{H_2}$ is in practice fixed at a value of less than or equal to $50 \times 10^5$ Pa, preferably between $5 \times 10^5$ and $30 \times 10^5$ Pa, and the reaction temperature is in practice fixed at a value of less than or equal to 150° C., preferably between room temperature and 120° C., in accordance with an advantageous arrangement of the invention.

These are mild conditions which are easy to employ and which make it possible to achieve hydrochlorosilane yields of 70% for a quantitative conversion of the disilanes with reaction times of less than a few hours.

The catalytic hydrogenation process in accordance with the invention proved to be particularly well suited to starting polysilanes (I) formed by one or more of the following compounds: $(CH_3)Cl_2Si—SiCl(CH_3)_2$ [$Me_{12}$]; $(CH_3)Cl_2Si—SiCl_2(CH_3)$ [$Me_{11}$]; $(CH_3)Cl_2Si—Si(CH_3)_3$ [$Me_{13}$]; $(CH_3)_2ClSi—SiCl(CH_3)_2$ [$Me_{22}$]; $(CH_3)Cl_2Si—SiCl(CH_3)—SiCl_2(CH_3)$ or $(CH_3)Cl_2Si—Si(CH_3)(SiCH_3Cl_2)—SiCl_2CH_3$.

In practice, the reaction medium, which is conventionally present in an autoclave with an atmosphere which has been "rendered inert", comprises nothing other than the starting polysilanes and the catalytic system AB. Means for introducing hydrogen under pressure are naturally provided, as well as means for heating and cooling the contents of the reactor.

The present invention will be better understood with the help of the examples which follow of carrying out a catalytic hydrogenolysis of a mixture $Me_{11}$, $Me_{12}$, $Me_{22}$, $Me_{13}$, with the help of a catalytic system AB in accordance with the invention under hydrogen pressure. These nonlimiting examples clearly reveal all the advantages of the process according to the invention and allow all the alternative embodiments which can be envisaged and which are covered by the invention to be anticipated.

EXAMPLES

Examples 1 to 14

The general procedure which will follow is applicable to the examples given in the following table. The dissolution aid B, the transition metal precursor A and 36 g of a mixture of disilanes: $(CH_3)Cl_2Si—SiCl_2(CH_3)_2$ [51.8%]; $(CH_3)_2ClSi—SiCl_2(CH_3)$ [27.9%]; $(CH_3)_2ClSi—SiCl(CH_3)_2$ [7.6%]; $(CH_3)_3Si—SiCl_2(CH_3)$ [2.1%] and other products in lower proportions having Si—O—Si and Si—CH$_2$—Si units [approximately 10%], are placed under an argon atmosphere in a 150 ml autoclave made of 316 stainless steel. After having purged the reactor under hydrogen, the mixture is placed under $30 \times 10^5$ Pa and then heated to the desired temperature (T). After a certain period of time as indicated in the table, the reactor is cooled to $-30°$ C. and samples of the medium are withdrawn for analysis by gas chromatography. The results of these analyses are given in the table below.

| Exs. | B nature | B mmol | A nature | A mmol | T °C. | Time (hours) | $Y_T$ mol % | $Y_H$ mol % | $S_H$ mol % | YIELDS mol % MeH$_2$ | Me$_2$H | MeH | Me$_3$ | Me | Me$_2$ |
|---|---|---|---|---|---|---|---|---|---|---|---|---|---|---|---|
| 1 | NBu$_4$Cl | 5.315 | None | 0 | 100 | 2.9 | 66.5 | 26.5 | 39.9 | 2 | 0 | 24.5 | 0.9 | 20.1 | 19 |
| 2 | None | 0.000 | NiCl$_2$ | 1.357 | 100 | 4 | 0 | 0 | 0 | 0 | 0 | 0 | 0 | 0 | 0 |
| 3 | NBu$_4$Cl | 5.981 | NiCl$_2$ | 1.311 | 100 | 0.2 | 99.5 | 66.8 | 67.1 | 13.4 | 1.7 | 51.7 | 0.6 | 12.4 | 19.7 |
| 4 | None | 0.000 | (NBu$_4$)$_2$NiCl$_4$ | 1.618 | 100 | 2 | 97.9 | 66 | 67.4 | 13 | 1 | 52.1 | 0 | 11.5 | 20.2 |
| 5 | NBu$_4$Cl | 3.271 | (NBu$_4$)$_2$NiCl$_4$ | 1.363 | 100 | 0.23 | 98.9 | 65 | 65.7 | 12.5 | 1.6 | 50.9 | 0.5 | 12.4 | 20.9 |
| 6 | PBu$_3$ | 7.287 | None | 0 | 100 | 6 | 63.5 | 22.4 | 35.3 | 0.6 | 0 | 21.8 | 1.7 | 28.6 | 10.5 |
| 7 | PBu$_3$ | 6.690 | NiCl$_2$ | 1.426 | 100 | 1.5 | 93.4 | 66 | 70.7 | 15.7 | 1 | 49.3 | 0.7 | 10.9 | 15.6 |
| 8a | None | 0.000 | (PBu$_3$)$_2$NiCl$_2$ | 0.939 | 100 | 1.5 | 4 | 0 | 0 | 0 | 0 | 0 | 0 | 1.1 | 3 |
| 8b | None | 0.000 | (PBu$_3$)$_2$NiCl$_2$ | 0.939 | 147 | 6.3 | 84.1 | 49.7 | 59 | 14.6 | 1.2 | 33.8 | 1 | 19.3 | 14.2 |
| 9 | NBu$_4$Cl | 6.99 | Ni powder[a] and gaseous HCl | 0.886 | 100 | 0.4 | 99 | 63.7 | 64.3 | 11 | 1.3 | 51.4 | 0 | 13.5 | 21.8 |
| 10 | NBu$_4$I | 5.580 | NiCl$_2$ | 1.519 | 100 | 1.5 | 87.5 | 53.7 | 61.4 | 8.2 | 0.9 | 44.6 | 0.8 | 12.1 | 20.9 |
| 11 | PPNCl[b] | 5.247 | NiCl$_2$ | 1.835 | 100 | 0.13 | 95.4 | 59.6 | 62.4 | 9.9 | 2.6 | 47 | 1 | 10.8 | 23.9 |
| 12 | NBu$_4$Cl | 6.020 | FeCl$_2$ | 1.400 | 100 | 5 | 97.3 | 67.4 | 69.3 | 14.6 | 1.9 | 51 | 0.8 | 10.6 | 18.4 |
| 13 | NBu$_4$Cl | 6.150 | CuCl$_2$ | 1.643 | 100 | 6.8 | 88.5 | 51.8 | 58.6 | 6.7 | 0.8 | 44.3 | 0.9 | 16.2 | 19.6 |
| 14 | NBu$_4$Cl | 5.685 | NiCl$_2$ | 1.36 | 70 | 1.3 | 95.0 | 68.0 | 71.6 | 13.1 | 2.2 | 52.7 | 1.0 | 10.6 | 15.2 |

[a] +8.3 mmol of gaseous HCl
[b] PPNCl corresponds to [(Ph)$_3$P=N=P(Ph)$_3$]Cl $Y_T$ = Yield of monosilanes (MeH$_2$ + Me$_2$H + MeH + Me$_3$ + Me + Me$_2$) calculated with regard to the Si introduced as molar % of the cleavable disilanes (Me$_{11}$ + Me$_{12}$ + Me$_{13}$)
$Y_H$ = Yield of hydrogenated monosilanes (MeH$_2$ + Me$_2$H + MeH) as molar % of the cleavable disilanes (Me$_{11}$ + Me$_{12}$ + Me$_{13}$)
$S_H$ = Selectivity for hydrogenated monosilanes = $Y_H/Y_T$
Yields expressed as molar % of the cleavable disilanes (Me$_{11}$ + Me$_{12}$ + Me$_{13}$)

Comments on the Examples

Examples 1 to 3 show the obvious advantage in using the catalytic system AB as described in the invention in comparison with the components A and B taken separately. Examples 2, 4 and 5 demonstrate that soluble nickel salts not possessing π-acceptor ligands are excellent precursors of the hydrogenation active catalyst. Examples 6 to 8 demonstrate that tributylphosphine can be used as solubilization aid but cannot be used as ligand of the transition metal salt A; if it is, a catalytic system is obtained with an activity which has become so weak (Ex. 8a and 8b) that it thereby becomes of little advantage. Example 9 shows that the component A can be obtained by in situ generation of the simple nickel salt by virtue of the action of hydrogen chloride on the powdered bulk metal. Examples 10 and 11 illustrate the fact that the solubilization aid can be another soluble halide or that the countercation of the halide is not necessarily tetrabutylammonium. Examples 12 and 13 prove that other simple transition metal salts can be used for the process. Finally, Example 14 shows that the process according to the invention can be carried out at much lower temperatures than those generally claimed in the prior state of the art without harming the most desired property, that is to say the manufacture of hydromethylchlorosilanes.

What is claimed is:

1. A process for the preparation of hydrosilanes from polysilanes, comprising contacting gaseous hydrogen under pressure with polysilanes of formula (I):

$$R_aH_bSi_nX_{2n+2-a-b} \tag{I}$$

in which:
- the R radicals are identical or different and are selected from the group comprising:
  linear or branched $C_1$–$C_6$ alkyls, aryls, linear or branched $C_1$–$C_6$ alkoxyls, a trifluoropropyl radical or a trimethylsiloxyl radical
- the X radicals are halogens which are identical to or different from one another
- n=2 to 20
- a=0 to 2n+2
- b=0 to 2n+2
- a+b=0 to 2n+2 in order to obtain monosilanes of formula (II):

$$R_cH_dSiX_{4-c-d} \tag{II}:$$

in which:
- R and X are as defined above
- c=1, 2, 3 or 4
- d=0, 1 or 2
- c+d=2, 3 or 4 wherein polysilane (I) and hydrogen are brought into contact in the presence of a catalytic system comprising
—A— on the one hand, at least one precursor of at least one hydrogenation catalyst, this precursor A being selected from salts of at least one transition metal, the anionic or neutral ligands of which are devoid of 7-acceptor orbitals;
—B— and, on the other hand, at least one aid for dissolution of the precursor A in the reaction medium, this aid B being selected from nucleophiles which are soluble in an aprotic medium;
with the exclusion of a reducing agent.

2. The process according to claim 1, wherein the metal or metals included in catalyst A belong to the following group:
Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pr and Au.

3. The process according to claim 1, wherein catalyst A is obtained from a corrodable metallic precursor, which may or may not be supported, subjected to the corrosive action of at least one acid capable of providing non-π-acceptor ligand or ligands for the salt A, the metallic precursor advantageously being selected from the group consisting of: Co, Fe, Ni, Pd, Ag, Pt and Cu.

4. The process according to claim 1, wherein the catalyst A is formed by at least one of the salts from the group comprising:
$NiCl_2$, $CUCl_2$ and $FeCl_2$
and the aid B comprises at least one of the products selected from the group consisting of:
$NBu_4Cl$; $PBu_3$; $[(Ph)_3P=N=P(Ph_3)]$ Cl;
Bu=butyl, and Ph=phenyl.

5. The process according to claim 1, wherein the hydrogen gas pressure $P_{H2}$ is fixed at a value of less than or equal to $50 \times 10^5$ Pa and the reaction temperature is fixed at a value of less than or equal to 150° C.

6. The process according to claim 1, wherein the polysilanes (I) are formed by one or more of the following compounds:
$(CH_3)Cl_2Si$—$SiCl(CH_3)_2$; $(CH_3)Cl_2Si$—$SiCl_2(CH_3)$;
$(CH_3)Cl_2Si$—$Si(CH_3)_3$; $(CH_3)_2ClSi$—$SiCl(CH_3)_2$;
$(CH_3)Cl_2Si$—$SiCl(CH_3)$—$SiCl_2(CH_3)$ or
$(CH_3)Cl_2Si$—$Si(CH_3)(SiCH_3Cl_2)$—$SiCl_2CH_3$.

7. The process according to claim 1, wherein said precursor A is a halide.

8. The process according to claim 7, wherein said halide is a chloride.

9. The process according to claim 1, wherein said aid B is a salt comprising anionic or neutral ligands which are devoid of π-acceptor orbitals.

10. The process according to claim 9, wherein said air B is a soluble halide.

11. The process according to claim 10, wherein said aid B is a chloride.

12. The process according to claim 2, wherein said meal is Pt, Ti, Cr, Mn, Fe, Cu, Ag, Au or Ni.

13. The process according to claim 12, wherein said metal is Ni.

14. The process according to claim 5, wherein the hydrogen gas pressure $P_{H2}$ is between $5 \times 10^5$ and $30 \times 10^5$ Pa.

15. The process according to claim 5, wherein the reaction temperature is between room temperature and 120° C.

* * * * *